(12) United States Patent
Knisley

(10) Patent No.: US 10,106,893 B1
(45) Date of Patent: Oct. 23, 2018

(54) IRIDIUM PRECURSORS FOR ALD AND CVD THIN FILM DEPOSITION AND USES THEREOF

(71) Applicant: Applied Materials, Inc., Santa Clara, CA (US)

(72) Inventor: Thomas Knisley, Monroe, MI (US)

(73) Assignee: APPLIED MATERIALS, INC., Santa Clara, CA (US)

(*) Notice: Subject to any disclaimer, the term of this patent is extended or adjusted under 35 U.S.C. 154(b) by 0 days.

(21) Appl. No.: 15/482,110

(22) Filed: Apr. 7, 2017

(51) Int. Cl.
| | |
|---|---|
| *C23C 16/18* | (2006.01) |
| *C23C 16/455* | (2006.01) |
| *C07F 15/00* | (2006.01) |
| *C23C 16/02* | (2006.01) |
| *C23C 16/44* | (2006.01) |
| *H01L 21/02* | (2006.01) |
| *H01L 21/285* | (2006.01) |

(52) U.S. Cl.
CPC ...... *C23C 16/45553* (2013.01); *C07F 15/004* (2013.01); *C23C 16/02* (2013.01); *C23C 16/18* (2013.01); *C23C 16/4408* (2013.01); *C23C 16/45527* (2013.01); *H01L 21/0228* (2013.01); *H01L 21/02175* (2013.01); *H01L 21/02205* (2013.01); *H01L 21/28556* (2013.01); *H01L 21/28568* (2013.01)

(58) Field of Classification Search
CPC ...... C23C 16/18; C23C 16/02; C23C 16/4408
See application file for complete search history.

(56) References Cited

PUBLICATIONS

Tewes (Thesis; Iridium-catalyzed dehydrogenation of alcohols; 2009).*

Knisley (New precursors and chemistry for the growth of transition metal films by atomic layer deposition; 2012).*

* cited by examiner

*Primary Examiner* — Pancham Bakshi
(74) *Attorney, Agent, or Firm* — Servilla Whitney LLC

(57) ABSTRACT

Metal coordination complexes comprising an iridium atom coordinated to at least one diazabutadiene based ligand having a structure represented by:

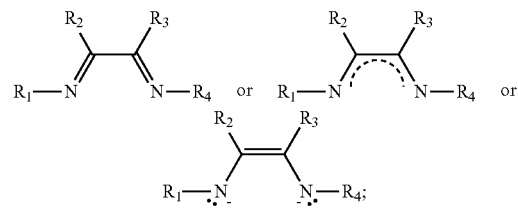

where R1 and R4 are independently selected from the group consisting of C1-C4 alkyl and amino groups, and each of R2 and R3 are independently selected from the group consisting of H, C1-C3 alkyl, or amino groups are described. Processing methods using the metal coordination complexes are also described.

5 Claims, 1 Drawing Sheet

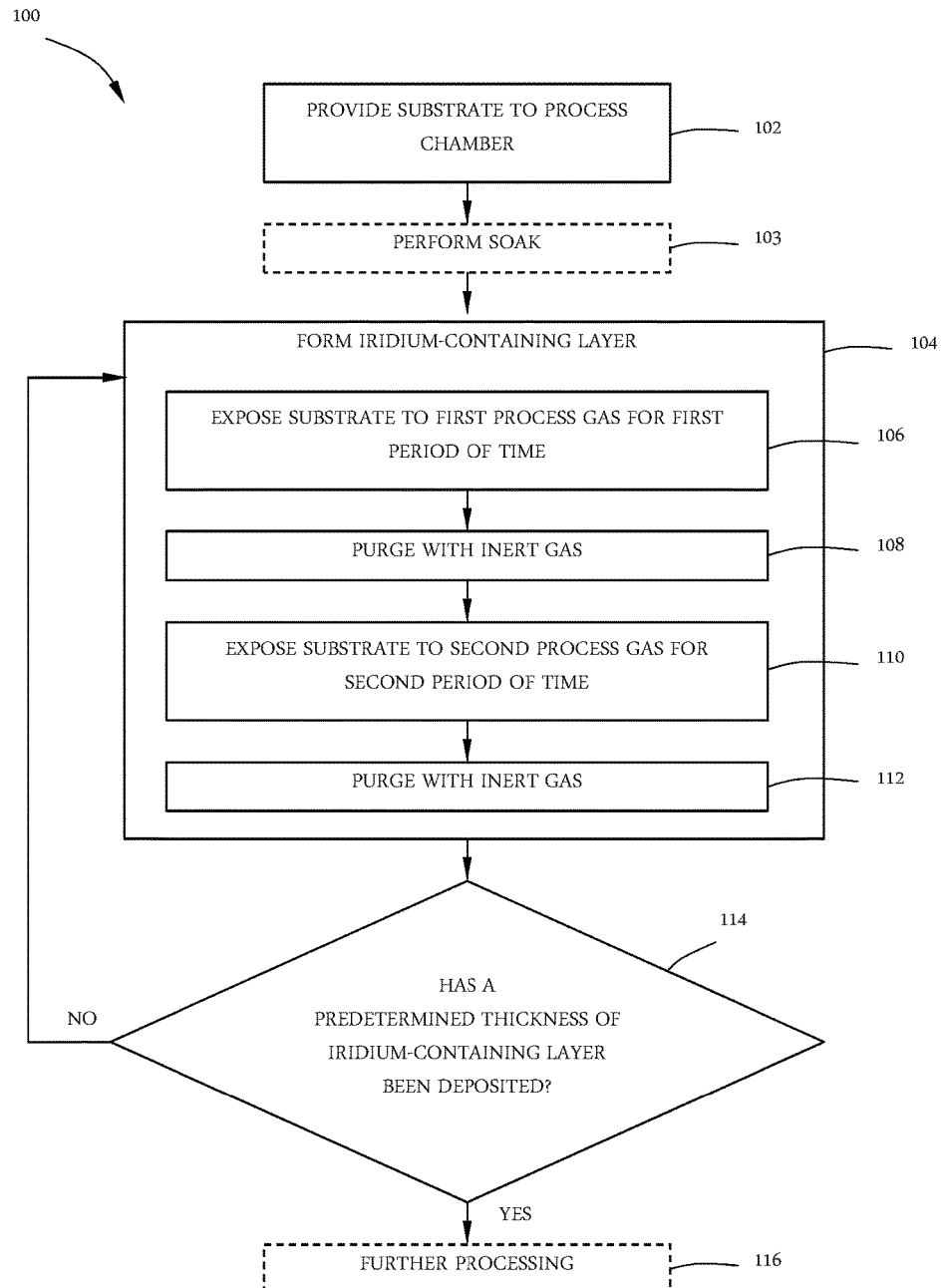

IRIDIUM PRECURSORS FOR ALD AND CVD THIN FILM DEPOSITION AND USES THEREOF

FIELD

Embodiments of the disclosure relate to iridium precursors for thin film deposition. More particularly, embodiments of the disclosure are directed to iridium precursors containing diazabutadiene ligands and methods of use.

BACKGROUND

The semiconductor industry continues to strive for continuous device miniaturization that is driven by the need for mobile, and high-performance systems in emerging industries such as autonomous vehicles, virtual reality, and future mobile devices. To accomplish this feat, new, high-performance materials are needed to circumvent inherent engineering and physics issues encountered in rapid reduction of features in microelectronic devices.

Iridium is a new proposed material for integration owing to its high melting point (ability to withstand high current densities), exceptional density, and ability to conduct electrical current. Iridium and iridium based thin films have attractive material and conductive properties. Iridium films have been proposed for applications from front end to back end parts of semiconductor and microelectronic devices.

Thin-films of iridium would ideally be deposited using thin-film deposition techniques such as Chemical Vapor Deposition (CVD) and Atomic Layer Deposition (ALD) owing to their inherent ability to deposit material in a high-throughput, conformal, and precise fashion.

Chemical vapor deposition (CVD) is one of the most common deposition processes employed for depositing layers on a substrate. CVD is a flux-dependent deposition technique that uses precise control of the substrate temperature and the precursors introduced into the processing chamber in order to produce a desired layer of uniform thickness. The reaction parameters become more critical as substrate size increases, creating a need for more complexity in chamber design and gas flow technique to maintain adequate uniformity.

A variant of CVD that demonstrates excellent step coverage is cyclical deposition or atomic layer deposition (ALD). Cyclical deposition is based upon atomic layer epitaxy (ALE) and employs chemisorption techniques to deliver precursor molecules on a substrate surface in sequential cycles. The cycle exposes the substrate surface to a first precursor, a purge gas, a second precursor and the purge gas. The first and second precursors react to form a product compound as a film on the substrate surface. The cycle is repeated to form the layer to a desired thickness.

Processing an iridium precursor often involves using oxygen or an oxidizing co-reagent. Use of oxygen and oxidizing co-reagents can be incompatible with other adjacent films in the device stack. Therefore, there is a need in the art for iridium precursors and co-reagents that react to form iridium metal and iridium based thin films without an oxidizing co-reagent.

The advancing complexity of advanced microelectronic devices is placing stringent demands on currently used deposition techniques. Unfortunately, there is a limited number of viable chemical precursors available that have the requisite properties of robust thermal stability, high reactivity, and vapor pressure suitable for film growth to occur.

In addition, precursors that often meet these properties still suffer from poor long-term stability and lead to thin films that contain elevated concentrations of contaminants such as oxygen, nitrogen, and/or halides that are often deleterious to the target film application. Therefore, there is a need for improved thin film precursors for iridium.

SUMMARY

One or more embodiments of the disclosure are directed to metal coordination complexes of the general formula $Ir(DAD0)_a X_d Y_e$ wherein DAD0 is a neutral diazadiene based ligand

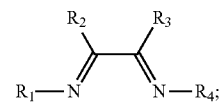

R1 and R4 are independently selected from the group consisting of C1-C4 alkyl and amino groups; each of R2 and R3 are independently selected from the group consisting of H, C1-C3 alkyl, or amino groups; X is an anionic ligand; Y is a neutral ligand not based on DAD; and a is 1-4, d is 0-8, and e is 0-8, with the proviso that where Y is CO, a is not 1.

Additional embodiments of the disclosure are directed to a metal coordination complex of the general formula $Ir(DAD1)_b X_d Y_e$, wherein DAD1 is an anionic diazadiene radical based ligand

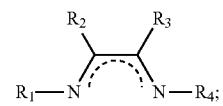

R1 and R4 are independently selected from the group consisting of C1-C4 alkyl and amino groups; each of R2 and R3 are independently selected from the group consisting of H, C1-C3 alkyl, or amino groups; X is an anionic ligand not based on DAD or a divalent DAD based ligand; Y is a neutral ligand not based on DAD, or a neutral DAD based ligand; and b is 1-4, d is 0-8 and e is 0-8, with the proviso that d and e are not both 0.

Further embodiments of the disclosure are directed to a metal coordination complex of the general formula $Ir(DAD2)_c X_d Y_e$, wherein DAD2 is a dianionic diazadiene based ligand

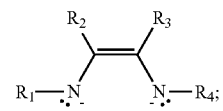

R1 and R4 are independently selected from the group consisting of C1-C4 alkyl and amino groups; each of R2 and R3 are independently selected from the group consisting of H, C1-C3 alkyl, or amino groups; X is an anionic ligand not based on DAD or a univalent DAD based ligand; Y is a neutral ligand not based on DAD or a neutral DAD based ligand; and c is 1-4, d is 0-8 and e is 0-8.

BRIEF DESCRIPTION OF THE DRAWING

So that the manner in which the above recited features of the disclosure can be understood in detail, a more particular description of the disclosure, briefly summarized above, may be had by reference to embodiments, some of which are illustrated in the appended drawings. It is to be noted, however, that the appended drawings illustrate only typical embodiments of the disclosure and are therefore not to be considered limiting of its scope, for the disclosure may admit to other equally effective embodiments.

The FIGURE illustrates an exemplary process sequence for the formation of a iridium layer using a two pulse cyclical deposition technique according to one embodiment described herein.

DETAILED DESCRIPTION

Embodiments of the disclosure provide precursors and processes for depositing iridium-containing films. The process of various embodiments uses vapor deposition techniques, such as an atomic layer deposition (ALD) or chemical vapor deposition (CVD) to provide iridium films.

A "substrate surface", as used herein, refers to any portion of a substrate or portion of a material surface formed on a substrate upon which film processing is performed. For example, a substrate surface on which processing can be performed include materials such as silicon, silicon oxide, silicon nitride, doped silicon, germanium, gallium arsenide, glass, sapphire, and any other materials such as metals, metal nitrides, metal alloys, and other conductive materials, depending on the application. Substrates include, without limitation, semiconductor wafers. Substrates may be exposed to a pretreatment process to polish, etch, reduce, oxidize, hydroxylate, anneal, UV cure, e-beam cure and/or bake the substrate surface. In addition to film processing directly on the surface of the substrate itself, in the present invention, any of the film processing steps disclosed may also be performed on an underlayer formed on the substrate as disclosed in more detail below, and the term "substrate surface" is intended to include such underlayer as the context indicates. Thus for example, where a film/layer or partial film/layer has been deposited onto a substrate surface, the exposed surface of the newly deposited film/layer becomes the substrate surface. Substrates may have various dimensions, such as 200 mm or 300 mm diameter wafers, as well as, rectangular or square panes. In some embodiments, the substrate comprises a rigid discrete material.

"Atomic layer deposition" or "cyclical deposition" as used herein refers to the sequential exposure of two or more reactive compounds to deposit a layer of material on a substrate surface. As used in this specification and the appended claims, the terms "reactive compound", "reactive gas", "reactive species", "precursor", "process gas" and the like are used interchangeably to mean a substance with a species capable of reacting with the substrate surface or material on the substrate surface in a surface reaction (e.g., chemisorption, oxidation, reduction). The substrate, or portion of the substrate, is exposed sequentially to the two or more reactive compounds which are introduced into a reaction zone of a processing chamber. In a time-domain ALD process, exposure to each reactive compound is separated by a time delay to allow each compound to adhere and/or react on the substrate surface and then be purged from the processing chamber. In a spatial ALD process, different portions of the substrate surface, or material on the substrate surface, are exposed simultaneously to the two or more reactive compounds so that any given point on the substrate is substantially not exposed to more than one reactive compound simultaneously. As used in this specification and the appended claims, the term "substantially" used in this respect means, as will be understood by those skilled in the art, that there is the possibility that a small portion of the substrate may be exposed to multiple reactive gases simultaneously due to diffusion, and that the simultaneous exposure is unintended.

In one aspect of a time-domain ALD process, a first reactive gas (i.e., a first precursor or compound A) is pulsed into the reaction zone followed by a first time delay. Next, a second precursor or compound B is pulsed into the reaction zone followed by a second delay. During each time delay, a purge gas, such as argon, is introduced into the processing chamber to purge the reaction zone or otherwise remove any residual reactive compound or reaction by-products from the reaction zone. Alternatively, the purge gas may flow continuously throughout the deposition process so that only the purge gas flows during the time delay between pulses of reactive compounds. The reactive compounds are alternatively pulsed until a desired film or film thickness is formed on the substrate surface. In either scenario, the ALD process of pulsing compound A, purge gas, compound B and purge gas is a cycle. A cycle can start with either compound A or compound B and continue the respective order of the cycle until achieving a film with the predetermined thickness.

In an embodiment of a spatial ALD process, a first reactive gas and second reactive gas (e.g., hydrogen radicals) are delivered simultaneously to the reaction zone but are separated by an inert gas curtain and/or a vacuum curtain. The substrate is moved relative to the gas delivery apparatus so that any given point on the substrate is exposed to the first reactive gas and the second reactive gas.

One or more embodiments of the disclosure are directed to a class of iridium metal coordination complexes with diazabutadiene ligands. In some embodiments, the iridium metal coordination complexes are used with a CVD or ALD process. In one or more embodiments, the diazabutadiene ligand is represented by the formula (I)

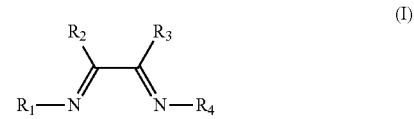

where each $R_1$ and $R_4$ are independently a C1-C4 alkyl or amino group and $R_2$ and $R_3$ are independently hydrogen or a C1-C3 alkyl or amino groups. As used in this manner, the letter "C" followed by a numeral (e.g., "C4") means that the substituent comprises the specified number of carbon atoms (e.g., C4 comprises four carbon atoms).

The diazabutadiene ligand can adopt several resonance forms when binding to a metal center as depicted in scheme (II).

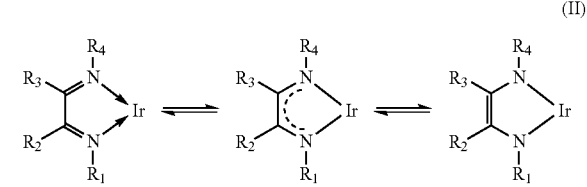

Each of these resonance forms imparts a different electronic charge on the iridium metal center when bonded together in a metal complex. The form on the left containing two double bonds (the diene) is a neutral, nonionic ligand (DAD0). The resonance form in the center of scheme (II) contains a radical resonance structure and is a monoanionic ligand (DAD1). The resonance form on the right of scheme (II) containing a single double bond is a dianionic ligand (DAD2).

In some embodiments, the complexes have the formula of $Ir(DAD0)_aX_dY_e$ containing from 1 to 4 neutral diazabutadiene ligands per metal center (i.e., a=1 to 4), where X is an anionic ligand and Y is a neutral ligand, a is 1 to 4, d is 0 to 8 and e is 0 to 8. In some embodiments, X can include DAD1 or DAD2. In some embodiments, when Y comprises CO, a is not 1, or a is greater than 1. In one or more embodiments, each of $R_1$ and $R_4$ are independently selected from the group consisting of C1 to C4 alkyl and amino groups. In some embodiments, each of $R_2$ and $R_3$ are independently selected from the group consisting of H, C1 to C3 alkyl, or amino groups.

The complex of formula $Ir(DAD0)_aX_dY_e$ may be a monomer or a dimer with metal-metal bonding or one or more ligands bridging the metal centers. Representative examples include, but are not limited to, structures illustrated in formulae (III) and (IV).

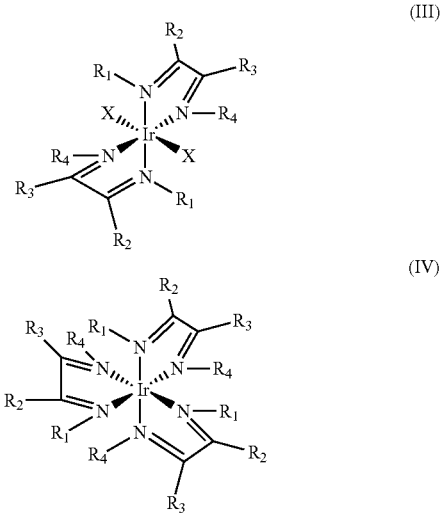

(III)

(IV)

In some embodiments, the complexes have the formula of $Ir(DAD1)_bX_dY_e$ containing from 1 to 4 anionic diazabutadiene radical ligands per metal center (i.e., b=1 to 4), where X is an anionic ligand, Y is a neutral ligand, b is 1 to 4, d is 0 to 8 and e is 0 to 8. In some embodiments, X is not based on a diazabutadiene backbone. In some embodiments, X comprises a divalent DAD based ligand (e.g., DAD2). In some embodiments, Y is not based on a diazabutadiene backbone. In some embodiments, Y comprises a neutral DAD based ligand (e.g., DAD0). In one or more embodiments, each of $R_1$ and $R_4$ are independently selected from the group consisting of C1 to C4 alkyl and amino groups. In some embodiments, each of $R_2$ and $R_3$ are independently selected from the group consisting of H, C1 to C3 alkyl, or amino groups.

The complex of the formula $Ir(DAD1)_bX_dY_e$ may be a monomer or a dimer with metal-metal bonding or one or more ligands bridging the metal centers. Representative examples include, but are not limited to, structures illustrated in formulae (V) and (VI).

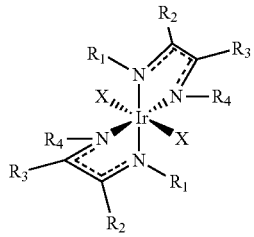

(V)

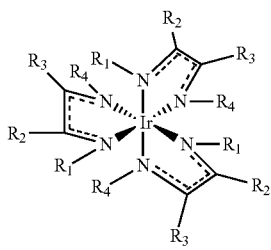

(VI)

In some embodiments, the complexes have the formula of $Ir(DAD2)_cX_dY_e$ containing from 1 to 4 dianionic diazabutadiene ligands per metal center (i.e., c=1 to 4), where X is an anionic ligand, Y is a neutral ligand, c is 1 to 4, d is 0 to 8 and e is 0 to 8. In some embodiments, X is not based on a diazabutadiene backbone. In some embodiments, X comprises a univalent DAD based ligand (e.g., DAD1). In some embodiments, Y is not based on a diazabutadiene backbone. In some embodiments, Y comprises a neutral DAD based ligand (e.g., DAD0). In one or more embodiments, each of $R_1$ and $R_4$ are independently selected from the group consisting of C1 to C4 alkyl and amino groups. In some embodiments, each of $R_2$ and $R_3$ are independently selected from the group consisting of H, C1 to C3 alkyl, or amino groups.

The complex of the formula $Ir(DAD2)_cX_dY_e$ may be a monomer or a dimer. A dimer may have metal-metal bonding or one or more ligands bridging the metal centers. Representative examples include, but are not limited to, structures illustrated in formulae (VII) and (VIII).

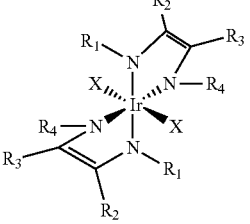

(VII)

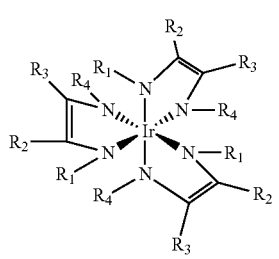

(VIII)

The inventor has found that having a non-hydrogen group as $R_2$ or $R_3$ helps to thermally stabilize the metal complex. In some embodiments, at least one of the $R_2$ or $R_3$ groups is not hydrogen. In one or more embodiments, at least one of R2 or R3 comprises an alkyl group having 1, 2, 3, 4 or 5 or more carbon atoms.

In some embodiments, the R1 and R4 groups are isopropyl groups and R2 and R3 are hydrogen. In some embodiments, d is 0 and e is in the range of 1 to 8. In some embodiments, d is in the range of 1 to 8 and e is 0. In some embodiments, d and e are 0.

The number of DAD based ligands, anionic ligands and neutral ligands can vary. In some embodiments, the combination of ligands results in a metal coordination complex in which the iridium atom has an oxidation state of neutral, +1, +2, +3, +4, +5, +6, +7, +8 or +9. In some embodiments, the iridium atom of the metal coordination complex has an oxidation state in the range of +2 to +6.

In some embodiments, the complex includes at least one anionic ligand (X). The anionic ligand of some embodiments comprises one or more of $F^-$, $Cl^-$, $Br^-$, $I^-$, $OH^-$ or $CN^-$. In some embodiments, the anionic ligand comprises one or more of DAD1 or DAD2.

In some embodiments, the complex includes at least one neutral donor ligand (Y). In some embodiments, the neutral donor ligand comprises a solvent molecule. The neutral donor ligand of some embodiments comprises one or more of $H_2O$, NO, $NR''_3$, $PR''_3$, dimethyl ether (DME), tetrahydrofuran (THF), tetramethylethylenediamine (TMEDA), CO, acetonitrile, pyridine, ammonia, ethylenediamine, and/or triphenylphosphine. where each R" is independently H, C1-C6 alkyl or aryl group. In some embodiments, the neutral donor ligand comprises one or more of DAD0.

Additional embodiments of the disclosure are directed to a metal coordination complex comprising an iridium atom and at least one diazadiene based neutral ligand.

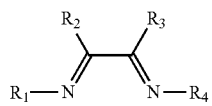

R1 and R4 are independently selected from the group consisting of C1-C4 alkyl and amino groups, each of R2 and R3 are independently selected from the group consisting of H, C1-C3 alkyl, amino groups or alkyl or aryl ring structures connecting R2 and R3.

Further embodiments of the disclosure are directed to a metal coordination complex comprising an iridium atom and at least one diazadiene based radical anions.

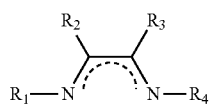

R1 and R4 are independently selected from the group consisting of C1-C4 alkyl and amino groups, each of R2 and R3 are independently selected from the group consisting of H, C1-C3 alkyl, amino groups or alkyl or aryl ring structures connecting R2 and R3.

Other embodiments of the disclosure are directed to a metal coordination complex comprising an iridium atom and at least one dianionic diazadiene based ligand

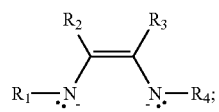

R1 and R4 are independently selected from the group consisting of C1-C4 alkyl and amino groups, each of R2 and R3 are independently selected from the group consisting of H, C1-C3 alkyl, amino groups or alkyl or aryl ring structures connecting R2 and R3.

The complexes of some embodiments may react as precursors in an ALD or CVD process to form thin films. Suitable reactants include, but are not limited to, $H_2$, $NH_3$, hydrazine, hydrazine derivatives and other co-reactants to make metal or $M_xN_y$ films. Suitable reactants also include, but are not limited to, $O_2$, $O_3$, water and other oxygen based co-reactants to make metal or $M_xO_y$ films. Plasma treatments of a co-reactant or as a post-treatment may also be used.

The FIGURE depicts a method for forming an iridium-containing layer on a substrate in accordance with one or more embodiment of the disclosure. The method 100 generally begins at 102, where a substrate, having a surface upon which an iridium-containing layer is to be formed is provided and placed into a processing chamber. As used herein, a "substrate surface" refers to any substrate surface upon which a layer may be formed. The substrate surface may have one or more features formed therein, one or more layers formed thereon, and combinations thereof. The substrate (or substrate surface) may be pretreated prior to the deposition of the iridium-containing layer, for example, by polishing, etching, reduction, oxidation, halogenation, hydroxylation, annealing, baking, or the like.

The substrate may be any substrate capable of having material deposited thereon, such as a silicon substrate, a III-V compound substrate, a silicon germanium (SiGe) substrate, an epi-substrate, a silicon-on-insulator (SOI) substrate, a display substrate such as a liquid crystal display (LCD), a plasma display, an electro luminescence (EL) lamp display, a solar array, solar panel, a light emitting diode (LED) substrate, a semiconductor wafer, or the like. In some embodiments, one or more additional layers may be disposed on the substrate such that the iridium-containing layer may be at least partially formed thereon. For example, in some embodiments, a layer comprising a metal, a nitride, an oxide, or the like, or combinations thereof may be disposed on the substrate and may have the iridium containing layer formed upon such layer or layers.

In some embodiments, the substrate may be exposed to an optional soak process 103 prior to beginning the cyclical deposition process to form an iridium-containing layer on the substrate (as discussed below at 104), as shown in phantom at 103. In one or more embodiments, the method of depositing the iridium-containing layer on the substrate 104 does not include a soaking process.

At 104, an iridium-containing layer is formed on the substrate. The iridium-containing layer may be formed via a cyclical deposition process, such as atomic layer deposition (ALD), or the like. In some embodiments, the forming of an iridium-containing layer via a cyclical deposition process may generally comprise exposing the substrate to two or more process gases sequentially. In time-domain ALD embodiments, exposure to each of the process gases are separated by a time delay/pause to allow the components of the process gases to adhere and/or react on the substrate surface. Alternatively, or in combination, in some embodiments, a purge may be performed before and/or after the exposure of the substrate to the process gases, wherein an inert gas is used to perform the purge. For example, a first process gas may be provided to the process chamber followed by a purge with an inert gas. Next, a second process gas may be provided to the process chamber followed by a purge with an inert gas. In some embodiments, the inert gas may be continuously provided to the process chamber and the first process gas may be dosed or pulsed into the process chamber followed by a dose or pulse of the second process gas into the process chamber. In such embodiments, a delay or pause may occur between the dose of the first process gas and the second process gas, allowing the continuous flow of inert gas to purge the process chamber between doses of the process gases.

In spatial ALD embodiments, exposure to each of the process gases occurs simultaneously to different parts of the substrate so that one part of the substrate is exposed to the first reactive gas while a different part of the substrate is exposed to the second reactive gas (if only two reactive gases are used). The substrate is moved relative to the gas delivery system so that each point on the substrate is sequentially exposed to both the first and second reactive gases. In any embodiment of a time-domain ALD or spatial ALD process, the sequence may be repeated until a predetermined layer thickness is formed on the substrate surface.

A "pulse" or "dose" as used herein is intended to refer to a quantity of a source gas that is intermittently or non-continuously introduced into the process chamber. The quantity of a particular compound within each pulse may vary over time, depending on the duration of the pulse. A particular process gas may include a single compound or a mixture/combination of two or more compounds, for example, the process gases described below.

The durations for each pulse/dose are variable and may be adjusted to accommodate, for example, the volume capacity of the processing chamber as well as the capabilities of a vacuum system coupled thereto. Additionally, the dose time of a process gas may vary according to the flow rate of the process gas, the temperature of the process gas, the type of control valve, the type of process chamber employed, as well as the ability of the components of the process gas to adsorb onto the substrate surface. Dose times may also vary based upon the type of layer being formed and the geometry of the device being formed. A dose time should be long enough to provide a volume of compound sufficient to adsorb/chemisorb onto substantially the entire surface of the substrate and form a layer of a process gas component thereon.

The process of forming the iridium-containing layer at step 104 may begin by exposing the substrate to a first reactive gas. In some embodiments, the first reactive gas comprises an iridium precursor (also referred to as an iridium-containing gas, and the like) and is exposed to the substrate for a first period of time, as shown at 106.

The iridium-containing gas may be provided in one or more pulses or continuously. The flow rate of the iridium-containing gas can be any suitable flow rate including, but not limited to, flow rates is in the range of about 1 to about 5000 sccm, or in the range of about 2 to about 4000 sccm, or in the range of about 3 to about 3000 sccm or in the range of about 5 to about 2000 sccm. The iridium-containing gas can be provided at any suitable pressure including, but not limited to, a pressure in the range of about 5 mTorr to about 25 Torr, or in the range of about 100 mTorr to about 20 Torr, or in the range of about 5 Torr to about 20 Torr, or in the range of about 50 mTorr to about 2000 mTorr, or in the range of about 100 mTorr to about 1000 mTorr, or in the range of about 200 mTorr to about 500 mTorr.

The period of time that the substrate is exposed to the iridium-containing gas may be any suitable amount of time necessary to allow the iridium precursor to form an adequate nucleation layer atop the substrate surfaces. For example, the process gas may be flowed into the process chamber for a period of about 0.1 seconds to about 90 seconds. In some time-domain ALD processes, the iridium-containing gas is exposed the substrate surface for a time in the range of about 0.1 sec to about 90 sec, or in the range of about 0.5 sec to about 60 sec, or in the range of about 1 sec to about 30 sec, or in the range of about 2 sec to about 25 sec, or in the range of about 3 sec to about 20 sec, or in the range of about 4 sec to about 15 sec, or in the range of about 5 sec to about 10 sec.

In some embodiments, an inert gas may additionally be provided to the process chamber at the same time as the iridium-containing gas. The inert gas may be mixed with the iridium-containing gas (e.g., as a diluent gas) or separately and can be pulsed or of a constant flow. In some embodiments, the inert gas is flowed into the processing chamber at a constant flow in the range of about 1 to about 10000 sccm. The inert gas may be any inert gas, for example, such as argon, helium, neon, combinations thereof, or the like. In one or more embodiments, the iridium-containing gas is mixed with argon prior to flowing into the process chamber.

The temperature of the substrate during deposition can be controlled, for example, by setting the temperature of the substrate support or susceptor. In some embodiments the substrate is held at a temperature in the range of about 100° C. to about 600° C., or in the range of about 200° C. to about 525° C., or in the range of about 300° C. to about 475° C., or in the range of about 350° C. to about 450° C. In one or more embodiments, the substrate is maintained at a temperature less than about 475° C., or less than about 450° C., or less than about 425° C., or less than about 400° C., or less than about 375° C.

In addition to the foregoing, additional process parameters may be regulated while exposing the substrate to the iridium-containing process gas. For example, in some embodiments, the process chamber may be maintained at a pressure of about 0.2 to about 100 Torr, or in the range of about 0.3 to about 90 Torr, or in the range of about 0.5 to about 80 Torr, or in the range of about 1 to about 50 Torr.

Next, at 108, the process chamber (especially in time-domain ALD) may be purged using an inert gas. (This may not be needed in spatial ALD processes as there is a gas curtain separating the reactive gases.) The inert gas may be any inert gas, for example, such as argon, helium, neon, or the like. In some embodiments, the inert gas may be the same, or alternatively, may be different from the inert gas provided to the process chamber during the exposure of the substrate to the first process gas at 106. In embodiments where the inert gas is the same, the purge may be performed by diverting the first process gas from the process chamber, allowing the inert gas to flow through the process chamber, purging the process chamber of any excess first process gas components or reaction byproducts. In some embodiments, the inert gas may be provided at the same flow rate used in conjunction with the first process gas, described above, or in some embodiments, the flow rate may be increased or decreased. For example, in some embodiments, the inert gas may be provided to the process chamber at a flow rate of about 0 to about 10000 sccm to purge the process chamber. In spatial ALD, purge gas curtains are maintained between the flows of reactive gases and purging the process chamber may not be necessary. In some embodiments of a spatial ALD process, the process chamber or region of the process chamber may be purged with an inert gas.

The flow of inert gas may facilitate removing any excess first process gas components and/or excess reaction byproducts from the process chamber to prevent unwanted gas phase reactions of the first and second process gases. For example, the flow of inert gas may remove excess iridium-containing gas from the process chamber, preventing a reaction between the iridium precursor and a subsequent reactive gas.

Next, at 110, the substrate is exposed to a second process gas for a second period of time. The second process gas reacts with the iridium-containing compound on the substrate surface to create a deposited film. The second process gas can impact the resulting iridium film. For example, when the second process gas is $H_2$, an iridium film is deposited, but when the second reactive gas is silane or disilane, an iridium silicide film may be deposited.

In some embodiments, the second reactive gas comprises one or more of $H_2$, $NH_3$, hydrazine, hydrazine derivatives, or plasmas thereof. In some embodiments, the second reactive gas is selected to deposit a metal film (e.g., an iridium film) or a metal nitride (e.g., $Ir_xN_y$) on the substrate.

In some embodiments, the second reactive gas comprises one or more of $O_2$, $O_3$, $H_2O$, $NO_2$, $N_2O$, or plasmas thereof. In one or more embodiments, the second reactive gas is selected to deposit a metal oxide, metal nitride or metal oxynitride film.

In some embodiments, the second reactive gas comprises a compound selected to form a metal silicide, metal silicate, metal carbide, metal carbonitride, metal oxycarbide, metal oxycarbonitride, or a metal film including one or more of O, N, C, Si or B.

In some embodiments, the second reactive gas comprises hydrogen and the resulting film formed is an iridium film. The hydrogen gas may be supplied to the substrate surface at a flow rate greater than the iridium-containing gas concentration. In one or more embodiments, the flow rate of $H_2$ is greater than about 1 time that of the iridium-containing gas, or about 100 times that of the iridium-containing gas, or in the range of about 3000 to 5000 times that of the iridium-containing gas. The hydrogen gas can be supplied, in time-domain ALD, for a time in the range of about 1 sec to about 30 sec, or in the range of about 5 sec to about 20 sec, or in the range of about 10 sec to about 15 sec. The hydrogen gas can be supplied at a pressure in the range of about 1 Torr to about 30 Torr, or in the range of about 5 Torr to about 25 Torr, or in the range of about 10 Torr to about 20 Torr, or up to about 50 Torr. The substrate temperature can be maintained at any suitable temperature. In one or more embodiments, the substrate is maintained at a temperature less than about 475° C., or at a temperature about the same as that of the substrate during the iridium-containing film deposition.

In some embodiments, the second reactive gas comprises hydrogen radicals. The hydrogen radicals can be generated by any suitable means including exposure of hydrogen gas to a "hot-wire". As used in this specification and the appended claims, the term "hot-wire" means any element that can be heated to a temperature sufficient to generate radicals in a gas flowing about the element. This is also referred to as a heating element.

The second reactive gas (e.g., hydrogen), while passing the hot wire, or heating element, becomes radicalized. For example, $H_2$ passing a hot ruthenium wire can result in the generation of H*. These hydrogen radicals are more reactive than ground state hydrogen atoms.

Next, at 112, the process chamber may be purged using an inert gas. The inert gas may be any inert gas, for example, such as argon, helium, neon, or the like. In some embodiments, the inert gas may be the same, or alternatively, may be different from the inert gas provided to the process chamber during previous process steps. In embodiments where the inert gas is the same, the purge may be performed by diverting the second process gas from the process chamber, allowing the inert gas to flow through the process chamber, purging the process chamber of any excess second process gas components or reaction byproducts. In some embodiments, the inert gas may be provided at the same flow rate used in conjunction with the second process gas, described above, or in some embodiments, the flow rate may be increased or decreased. For example, in some embodiments, the inert gas may be provided to the process chamber at a flow rate of greater than 0 to about 10,000 sccm to purge the process chamber.

While the generic embodiment of the processing method shown in the FIGURE includes only two pulses of reactive gases, it will be understood that this is merely exemplary and that additional pulses of reactive gases may be used. For example, a nitride film of some embodiments can be grown by a first pulse containing a precursor gas like iridium pentachloride, a second pulse with a reducing agent followed by purging and a third pulse for nitridation. The pulses can be repeated in their entirety or in part. For example all three pulses could be repeated or only two can be repeated. This can be varied for each cycle.

Next, at 114, it is determined whether the iridium-containing layer has achieved a predetermined thickness. If the predetermined thickness has not been achieved, the method 100 returns to 104 to continue forming the iridium-containing layer until the predetermined thickness is reached. Once the predetermined thickness has been reached, the method 100 can either end or proceed to 116 for optional further processing (e.g., bulk deposition of an iridium or other metal film). In some embodiments, the bulk deposition process may be a CVD process. Upon completion of deposition of the iridium-containing layer to a desired thickness, the method 100 generally ends and the substrate can proceed for any further processing. For example, in some embodiments, a CVD process may be performed to bulk deposit the iridium-containing layer to a target thickness. For example in some embodiments, the iridium-containing layer may be deposited via ALD or CVD reaction of the iridium precursor and hydrogen radicals to form a total layer thickness of about 10 to about 10,000 Å, or in some embodiments, about 10 to about 1000 Å, or in some embodiments, about 500 to about 5,000 Å.

Suitable co-reactants include, but are not limited to, hydrogen, ammonia, hydrazine, hydrazine derivatives, oxygen, ozone, water, peroxide, combinations and plasmas thereof. In some embodiments, the co-reactant comprises one or more of $NH_3$, hydrazine, hydrazine derivatives, $NO_2$, combinations thereof, plasmas thereof and/or nitrogen plasma to deposit a metal nitride film (e.g., $Ir_xN_y$). In some embodiments, the co-reactant comprises one or more of $O_2$, $O_3$, $H_2O_2$, water, plasmas thereof and/or combinations thereof to deposit a metal oxide film (e.g., $Ir_xO_y$). In some embodiments, the coreactant comprises one or more of $H_2$, hydrazine, combinations thereof, plasmas thereof, argon plasma, nitrogen plasma, helium plasma, $Ar/N_2$ plasma, Ar/He plasma, $N_2$/He plasma and/or $Ar/N_2$/He plasma to deposit a metal film (e.g., Ir).

Some embodiments of the disclosure are directed to iridium precursors and methods of depositing iridium containing films. The iridium containing films of some embodiments comprises one or more of iridium metal, iridium silicate, iridium oxide, iridium nitride, iridium carbide, iridium boride, iridium oxynitride, iridium oxycarbide, iridium oxyboride, iridium carbonitride, iridium borocarbide, iridium oxycarbonitride, iridium oxyboronitride and/or iridium oxyborocarbonitride. Those skilled in the art will understand that the film deposited may have a nonstoichiometric amount of metal, oxygen, nitrogen, carbon and/or boron atoms on an atomic basis. Boron and/or carbon atoms can be incorporated from the metal precursor or the reactant.

In some embodiments, the iridium-containing film comprises greater than or equal to about 95 atomic percent iridium. In one or more embodiments, the sum of C, N, O and halogen atoms is less than or equal to about 5 atomic percent of the iridium-containing film.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A metal coordination complex of the general formula $Ir(DAD1)_b X_d Y_e$, wherein:

DAD1 is an anionic diazadiene radical based ligand

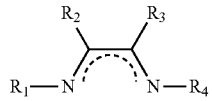

where R1 and R4 are independently selected from the group consisting of C1-C4 alkyl and amino groups;
each of R2 and R3 are independently selected from the group consisting of H, C1-C3 alkyl, or amino groups;
X is an anionic ligand not based on DAD or a divalent DAD based ligand;
Y is a neutral ligand not based on DAD, or a neutral DAD based ligand; and
b is 1-4, d is 0-8 and e is 0-8,
with the proviso that d and e are not both 0.

2. The metal coordination complex of claim 1, wherein the iridium atom has an oxidation state of neutral, +1, +2, +3, +4, +5, +6, +7, +8 or +9.

3. A method of depositing an iridium containing film on a substrate surface, the method comprising exposing the substrate surface to the metal coordination complex of claim 1 and a reactant.

4. A metal coordination complex of the general formula $Ir(DAD1)_b X_d Y_e$, wherein:

DAD1 is an anionic diazadiene radical based ligand

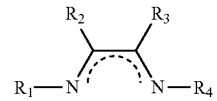

where R1 and R4 are independently selected from the group consisting of C1-C4 alkyl and amino groups;
each of R2 and R3 are independently selected from the group consisting of H, C1-C3 alkyl, or amino groups;
X is one or more of $F^-$, $Cl^-$, $Br^-$, $I^-$, $OH^-$, or $CN^-$;
Y is a neutral ligand not based on DAD, or a neutral DAD based ligand; and
b is 1-4, d is 0-8 and e is 0-8,
with the proviso that d and e are not both 0.

5. A metal coordination complex of the general formula $Ir(DAD1)_b X_d Y_e$, wherein:

DAD1 is an anionic diazadiene radical based ligand

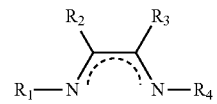

where R1 and R4 are independently selected from the group consisting of C1-C4 alkyl and amino groups;
each of R2 and R3 are independently selected from the group consisting of H, C1-C3 alkyl, or amino groups;
X is an anionic ligand not based on DAD or a divalent DAD based ligand;
Y is one or more of $H_2O$, $NH_3$, CO, NO, $NR''_3$, $PR''_3$, dimethyl ether (DME), tetrahydrofuran (THF), tetramethylethylenediamine (TMEDA), acetonitrile, pyridine, ethylenediamine, or triphenylphosphine, and each R" is independently H, C1-C6 alkyl or aryl group; and
b is 1-4, d is 0-8 and e is 0-8,
with the proviso that d and e are not both 0.

* * * * *